US009687273B2

(12) United States Patent
Henzler et al.

(10) Patent No.: US 9,687,273 B2
(45) Date of Patent: Jun. 27, 2017

(54) ENDOSCOPIC SURGICAL INSTRUMENTS AND RELATED METHODS

(71) Applicant: Gimmi GmbH, Tuttlingen (DE)

(72) Inventors: Thilo Henzler, Tuttlingen (DE); Steve Eubanks, Winter Park, FL (US); Wayne Shortt, Salt Lake City, UT (US)

(73) Assignee: Gimmi GmbH, Tuttlingen (DE)

( * ) Notice: Subject to any disclaimer, the term of this patent is extended or adjusted under 35 U.S.C. 154(b) by 5 days.

(21) Appl. No.: 14/481,811

(22) Filed: Sep. 9, 2014

(65) Prior Publication Data

US 2015/0133736 A1    May 14, 2015

Related U.S. Application Data

(60) Provisional application No. 61/876,452, filed on Sep. 11, 2013.

(51) Int. Cl.
| | | |
|---|---|---|
| A61B 17/34 | (2006.01) | |
| A61B 17/02 | (2006.01) | |
| A61B 1/00 | (2006.01) | |
| A61B 17/29 | (2006.01) | |
| A61B 17/00 | (2006.01) | |

(52) U.S. Cl.
CPC ...... *A61B 17/3498* (2013.01); *A61B 1/00068* (2013.01); *A61B 1/00135* (2013.01); *A61B 1/00137* (2013.01); *A61B 17/29* (2013.01); *A61B 17/3421* (2013.01); *A61B 17/3462* (2013.01); *A61B 2017/00336* (2013.01); *A61B 2017/347* (2013.01)

(58) Field of Classification Search
CPC .......... A61B 17/3498; A61B 2017/347; A61B 1/00135
See application file for complete search history.

(56) References Cited

U.S. PATENT DOCUMENTS

| | | |
|---|---|---|
| 1,294,284 A | 2/1919 | Logeman |
| 2,670,519 A | 10/1951 | Recklitis |
| 3,645,268 A | 2/1972 | Capote |
| 3,750,667 A | 8/1973 | Pshenichny et al. |
| 3,788,326 A | 1/1974 | Jacobs |
| 3,870,048 A | 3/1975 | Yoon |
| 3,955,578 A | 5/1976 | Chamness et al. |
| 4,174,715 A | 11/1979 | Hasson |

(Continued)

FOREIGN PATENT DOCUMENTS

| | | |
|---|---|---|
| CA | 2587007 | 5/2006 |
| DE | 2743336 A1 | 3/1979 |

(Continued)

*Primary Examiner* — Ellen C Hammond
(74) *Attorney, Agent, or Firm* — Thorpe North & Western, LLP

(57) ABSTRACT

A minimally invasive surgical system includes a surgical instrument having an elongate body portion and an oversleeve, through which the elongate body portion of the surgical instrument is extendable. A valve assembly is associated with one of the oversleeve or the surgical instrument. Mating structure is associated with two or more of the oversleeve, the surgical instrument and the valve assembly, the mating structure is operable to limit or prevent relative movement between the oversleeve and the surgical instrument.

4 Claims, 6 Drawing Sheets

(56) References Cited

U.S. PATENT DOCUMENTS

| | | |
|---|---|---|
| 4,230,123 A | 10/1980 | Hawkins, Jr. |
| 4,254,762 A | 3/1981 | Yoon |
| 4,393,872 A | 7/1983 | Reznik et al. |
| 4,633,860 A | 1/1987 | Korth et al. |
| 4,650,472 A | 3/1987 | Bates |
| 4,674,501 A | 6/1987 | Greenberg |
| 4,763,668 A | 8/1988 | Macek et al. |
| 4,815,476 A | 3/1989 | Clossick |
| 4,953,559 A | 9/1990 | Salerno |
| 4,955,890 A | 9/1990 | Yamamoto et al. |
| 5,098,439 A | 3/1992 | Hill et al. |
| 5,112,299 A | 5/1992 | Pascaloff |
| 5,127,393 A | 7/1992 | McFarlin et al. |
| 5,156,633 A | 10/1992 | Smith |
| 5,169,397 A | 12/1992 | Sakashita et al. |
| 5,178,607 A | 1/1993 | Lynn et al. |
| 5,190,528 A | 3/1993 | Fonger et al. |
| 5,255,691 A | 10/1993 | Otten |
| 5,263,959 A | 11/1993 | Fischell |
| 5,275,583 A | 1/1994 | Crainich |
| 5,275,612 A | 1/1994 | Bales, Jr. |
| 5,281,230 A | 1/1994 | Heidmueller |
| 5,295,977 A | 3/1994 | Cohen et al. |
| 5,322,055 A | 6/1994 | Davidson et al. |
| 5,324,301 A | 6/1994 | Drucker |
| 5,374,252 A | 12/1994 | Banks et al. |
| 5,376,094 A | 12/1994 | Kline |
| 5,380,292 A | 1/1995 | Wilson |
| 5,385,572 A | 1/1995 | Nobles et al. |
| 5,419,339 A | 5/1995 | Palmer |
| 5,456,673 A | 10/1995 | Ziegler et al. |
| 5,575,804 A | 11/1996 | Yoon |
| 5,593,420 A | 1/1997 | Eubanks, Jr et al. |
| 5,607,440 A | 3/1997 | Danks et al. |
| 5,630,822 A | 5/1997 | Hermann et al. |
| 5,643,301 A | 7/1997 | Mollenauer |
| 5,669,883 A | 9/1997 | Arias et al. |
| 5,688,246 A | 11/1997 | Waitz et al. |
| 5,843,108 A | 12/1998 | Samuels |
| 5,843,115 A | 12/1998 | Morejon |
| 5,899,919 A | 5/1999 | Eubanks, Jr. et al. |
| 6,136,014 A | 10/2000 | Sirimanne et al. |
| 6,165,184 A | 12/2000 | Verdura et al. |
| 6,187,022 B1 | 2/2001 | Alexander et al. |
| 6,716,201 B2 | 4/2004 | Blanco |
| 2002/0007152 A1 | 1/2002 | Hermann et al. |
| 2002/0026207 A1 | 2/2002 | Stellon et al. |
| 2002/0133188 A1 | 9/2002 | O'Heeron et al. |
| 2002/0161387 A1 | 10/2002 | Blanco |
| 2002/0193806 A1 | 12/2002 | Moenning et al. |
| 2003/0073960 A1 | 4/2003 | Adams |
| 2005/0177183 A1 | 8/2005 | Thorne et al. |
| 2006/0030870 A1 | 2/2006 | Staudner |
| 2006/0276772 A1 | 12/2006 | Moos et al. |
| 2007/0213766 A1* | 9/2007 | Ravikumar .......... A61B 17/221 606/205 |
| 2007/0250112 A1* | 10/2007 | Ravikumar .......... A61B 17/221 606/205 |
| 2007/0260274 A1 | 11/2007 | Heinen |
| 2009/0125037 A1* | 5/2009 | Goto ................ A61B 1/00087 606/140 |
| 2009/0209913 A1* | 8/2009 | Ferrari ................ A61B 17/02 604/165.04 |
| 2009/0326463 A1* | 12/2009 | Ross .................. A61B 17/3423 604/167.01 |
| 2011/0092910 A1* | 4/2011 | Schultz .............. A61B 17/3415 604/165.04 |
| 2014/0024896 A1 | 1/2014 | West |
| 2015/0272618 A1* | 10/2015 | Fung .................. A61B 17/3478 606/185 |

FOREIGN PATENT DOCUMENTS

| | | |
|---|---|---|
| DE | 4320008 | 3/1994 |
| DE | 4238596 | 6/1994 |
| FR | 2595237 | 9/1987 |
| GB | 2199247 | 7/1988 |
| GB | 2400324 A | 10/2004 |

* cited by examiner

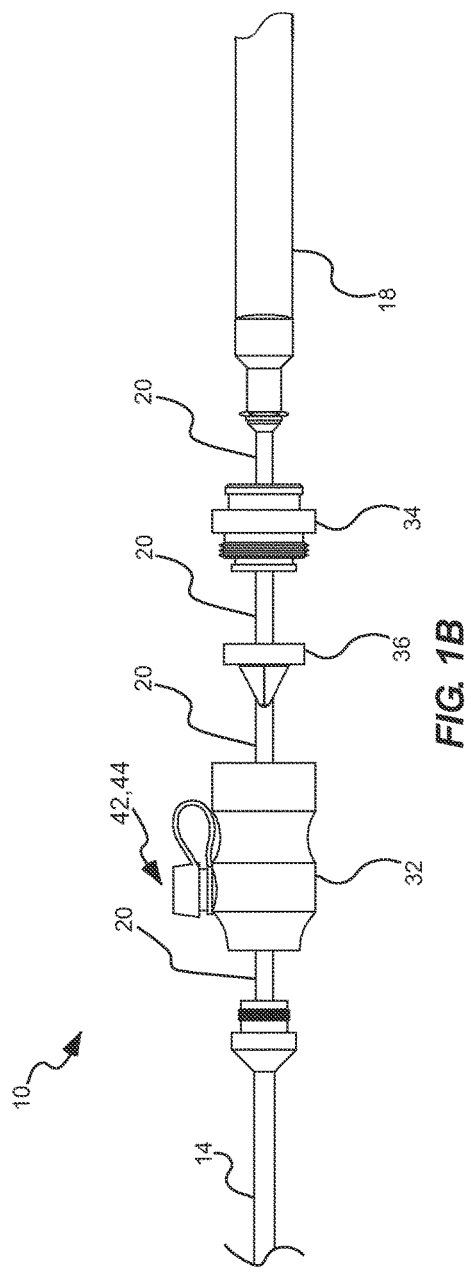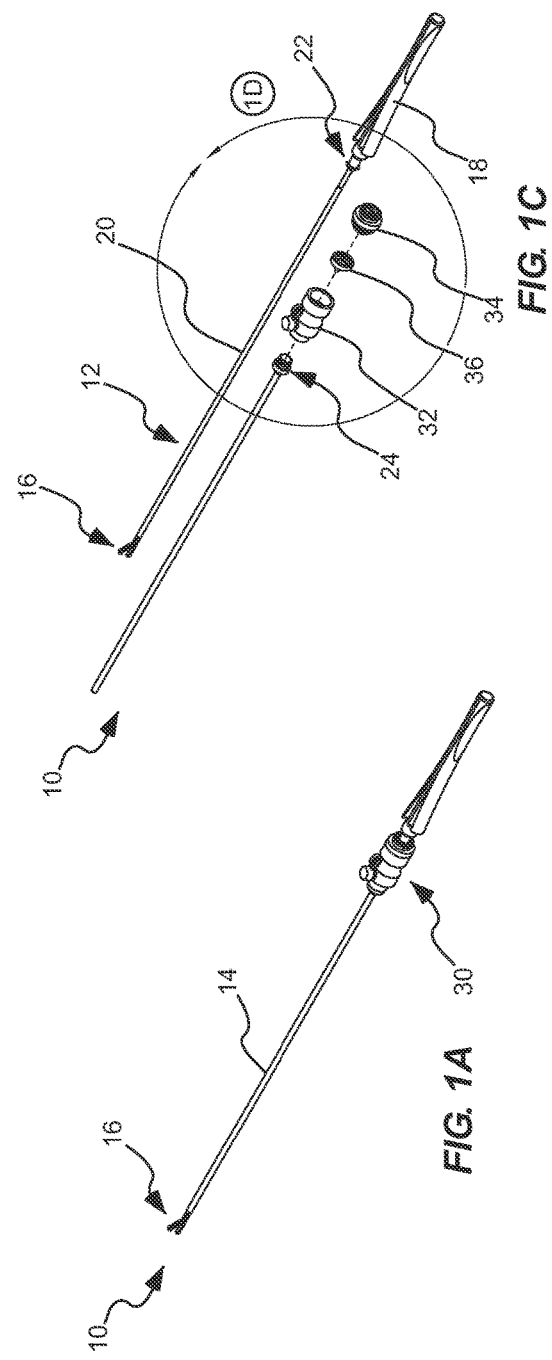

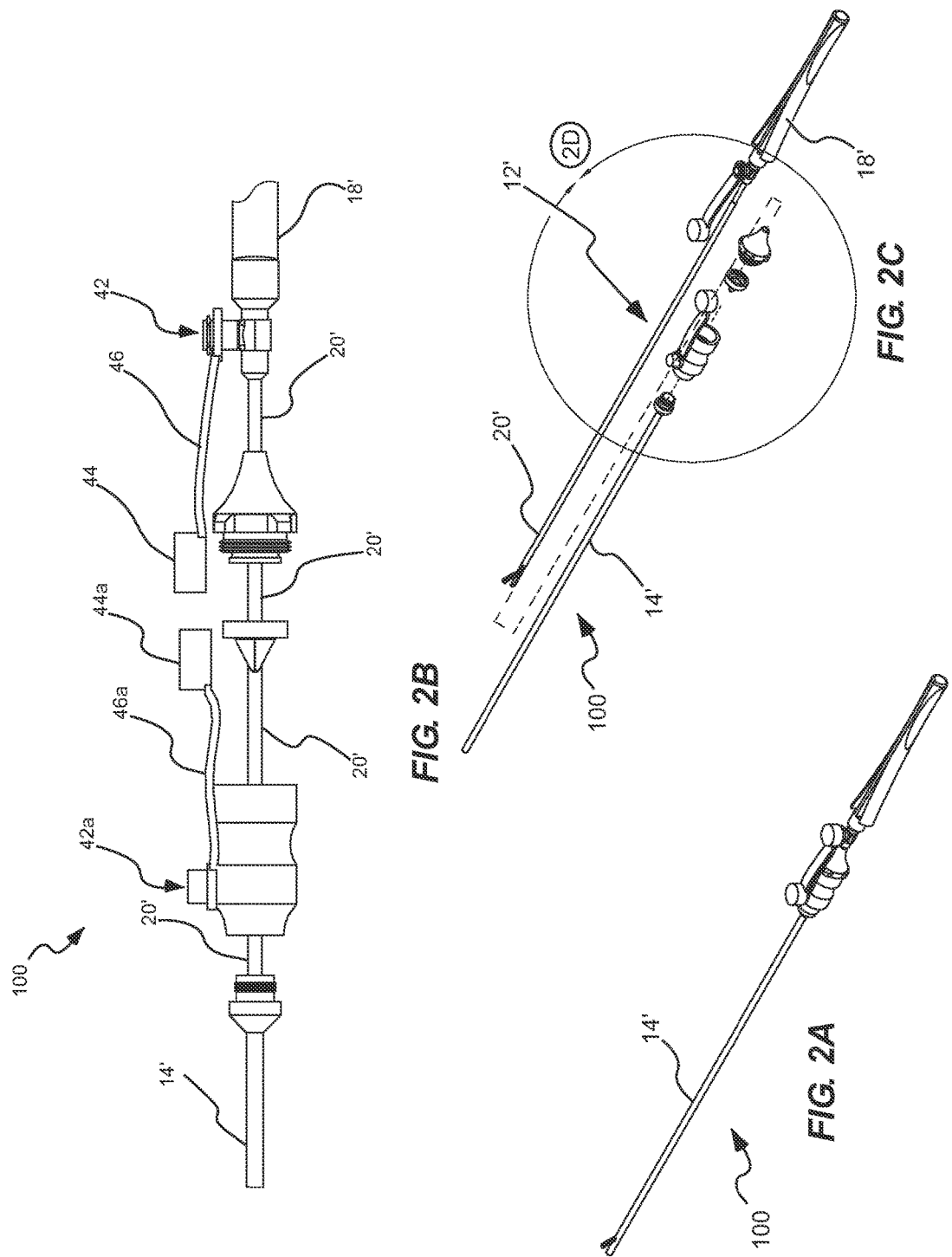

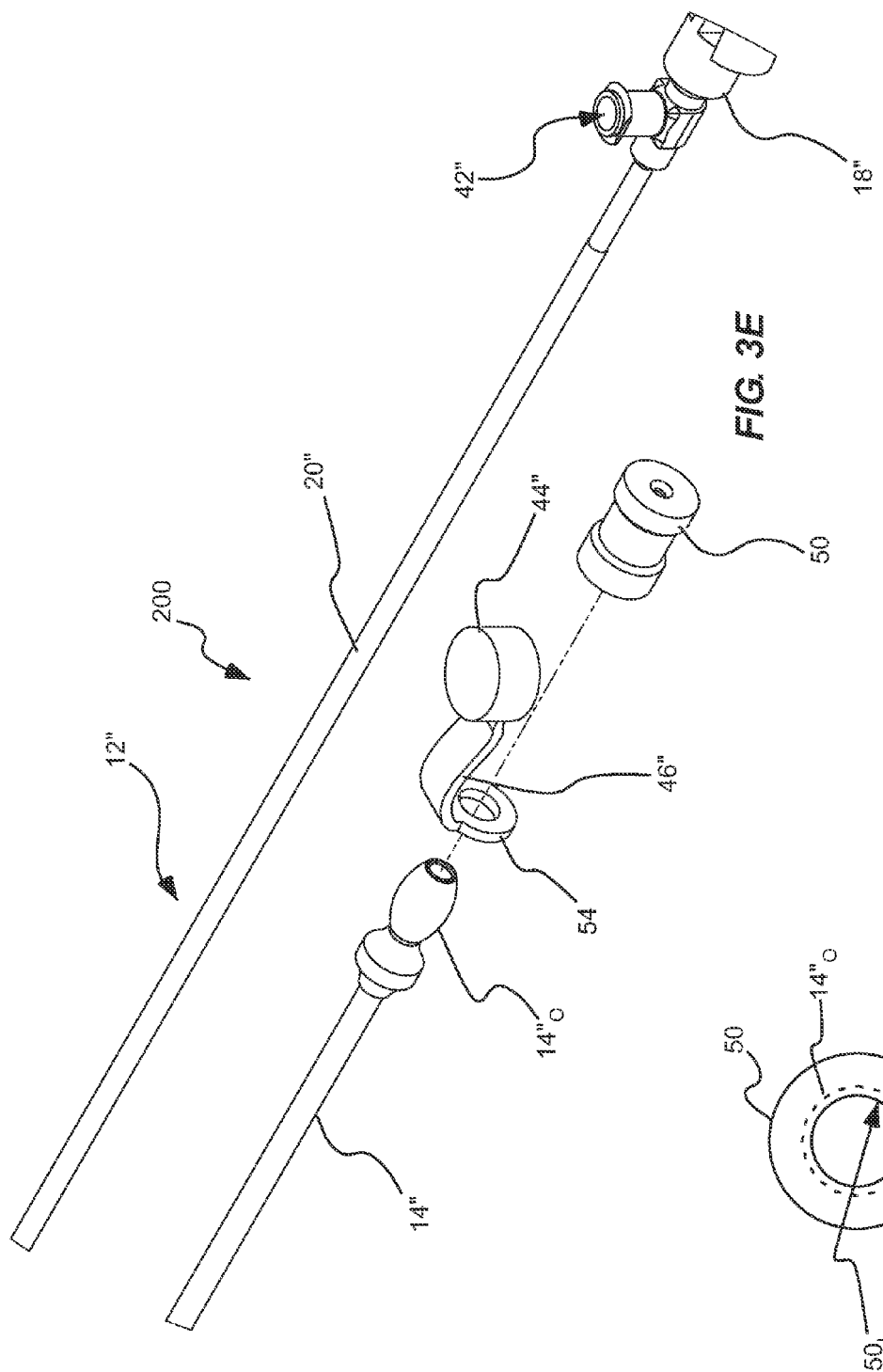

ENDOSCOPIC SURGICAL INSTRUMENTS AND RELATED METHODS

PRIORITY CLAIM

Priority is claimed of and to U.S. Provisional Patent Application Ser. No. 61/876,452, filed Sep. 11, 2013, which is hereby incorporated herein by reference in its entirety.

BACKGROUND OF THE INVENTION

Field of the Invention

The present invention relates generally to the field of endoscopic surgery. More particularly, the present invention relates to endoscopic surgical instruments for use in minimally invasive surgical procedures. Related methods utilizing the surgical instruments are also disclosed.

Related Art

The general field of endoscopic surgical procedures is generally directed to minimally-invasive surgical techniques that provide, in one manner or another, access to an internal organ or cavity of a patient's body. Examples of such procedures include, without limitation, thoracoscopy, laparoscopy, pelviscopy, endoscopy, and arthroscopy. Generally speaking, these procedures minimize trauma to a patient by providing access to interior body cavities through very small incisions. Oftentimes a percutaneous cannulas, known as a trocar sleeve, is used to provide a port for a generally elongated surgical instrument that is to be introduced into the patient. Laparoscopes, endoscopes, arthroscopes and the like can be used during these various procedures to provide visual observation of the procedure.

By obviating the need for a large, open incision to expose the body cavity, minimally-invasive techniques can significantly reduce the pain, recovery period, morbidity, mortality rates, and the cost associated with open surgical procedures.

SUMMARY OF THE INVENTION

In accordance with one aspect of the invention, a minimally invasive surgical system includes a surgical instrument having an elongate body portion; and an oversleeve, through which the elongate body portion of the surgical instrument can be extended. A valve assembly can be associated with one of the oversleeve or the surgical instrument. Mating structure can be associated with two or more of the oversleeve, the surgical instrument and the valve assembly, the mating structure being operable to limit or prevent relative movement between the oversleeve and the surgical instrument.

In accordance with another aspect of the invention, a minimally invasive surgical system is provided, including a surgical instrument having an elongate body portion and an oversleeve. The oversleeve can be positionable over the elongate body portion of the surgical instrument. A valve assembly can be associated with one of the oversleeve or the surgical instrument. The valve assembly can include: first and second end caps removably coupleable to one another; and a valve positioned between the first and second end caps, the valve operable to limit or prevent flow of fluid from the valve assembly from one end cap when the end caps are coupled to one another. One of the end caps can be coupleable to the surgical instrument, and another of the end caps being coupleable to the oversleeve. The valve assembly can be operable to limit or prevent relative movement between the oversleeve and the surgical instrument and to allow fluid flow through the valve assembly and into an internal portion of the oversleeve.

In accordance with another aspect of the invention, a method of limiting or preventing movement of an oversleeve relative to a surgical instrument is provided, including: coupling a valve assembly to an oversleeve, the valve assembling including therein a valve operable to limit or prevent fluid flow in at least one direction relative to the valve assembly; and coupling the valve assembly to a surgical instrument.

Additional features and advantages of the invention will be apparent from the detailed description which follows, taken in conjunction with the accompanying drawings, which together illustrate, by way of example, features of the invention.

BRIEF DESCRIPTION OF THE DRAWINGS

The following drawings illustrate exemplary embodiments for carrying out the invention. Like reference numerals refer to like parts in different views or embodiments of the present invention in the drawings.

FIG. 1A is a perspective view of an exemplary surgical instrument system in accordance with an embodiment of the invention;

FIG. 1B is a partially sectioned and exploded view of the system of FIG. 1A;

FIG. 1C is an exploded perspective view of the system of FIG. 1A;

FIG. 2A is a perspective view of another exemplary surgical instrument system in accordance with an embodiment of the invention;

FIG. 2B is a partially sectioned and exploded view of the system of FIG. 2A;

FIG. 2C is an exploded perspective view of the system of FIG. 2A;

FIG. 3D is an end view of a gasket of the system of FIG. 3A; and

FIG. 3E is a more detailed view of section 3E of FIG. 3E.

DETAILED DESCRIPTION

Figure 1D:
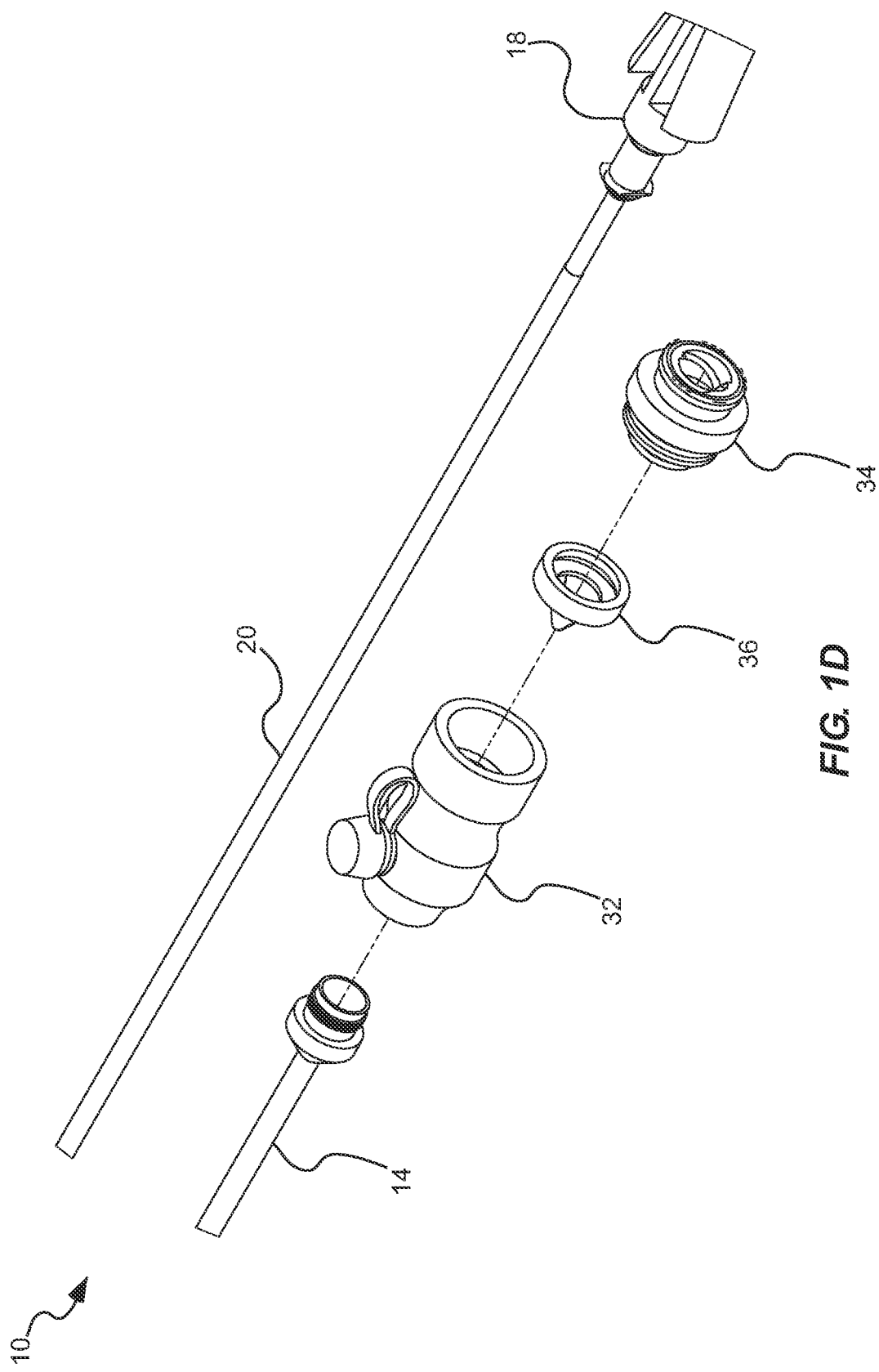
FIG. 1D is a more detailed view of section 1D of FIG. 1C.
Figure 2D:
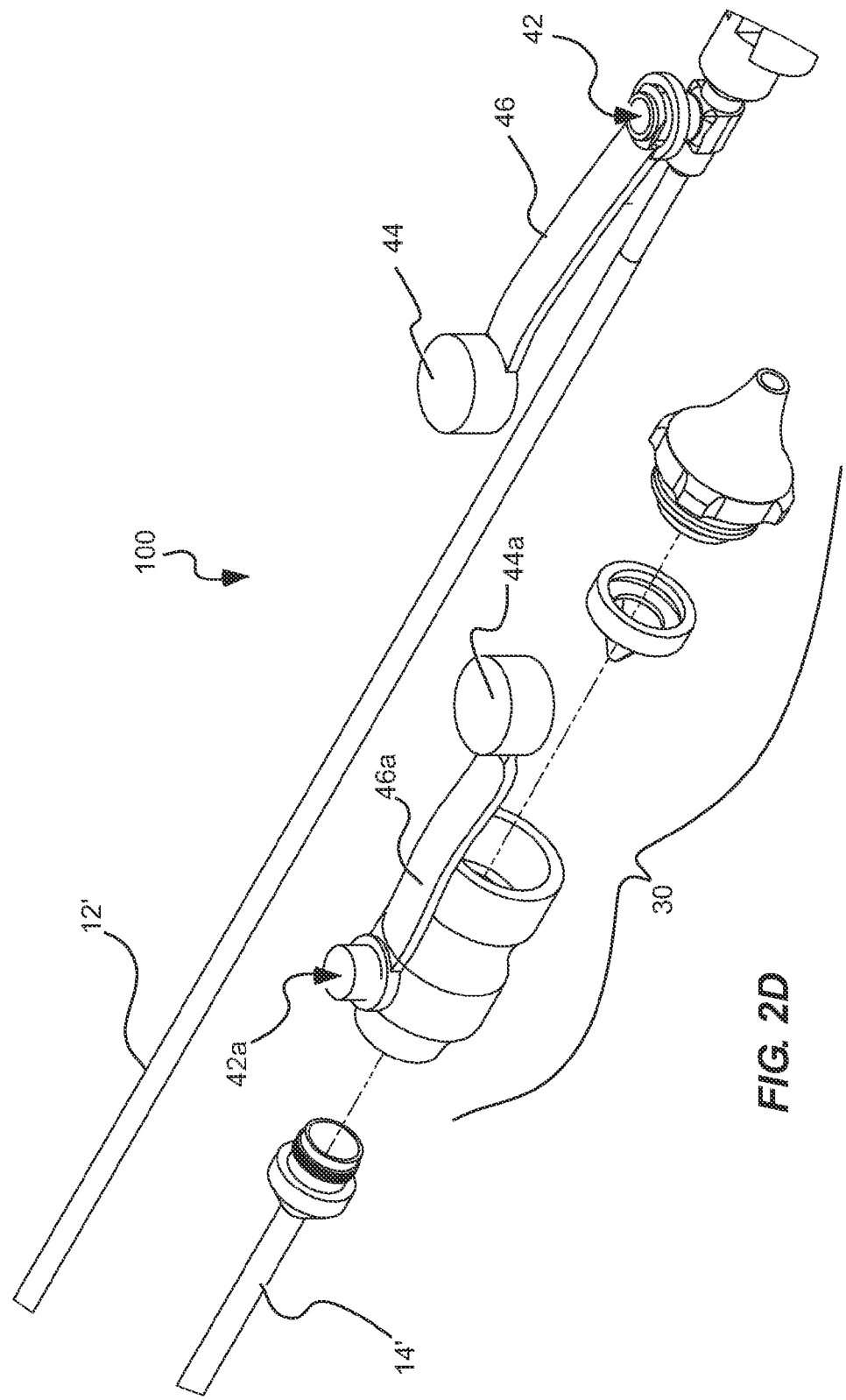
FIG. 2D is a more detailed view of section 1D of FIG. 2C.

Before the present invention is disclosed and described, it is to be understood that this invention is not limited to the particular structures, process steps, or materials disclosed herein, but is extended to equivalents thereof as would be recognized by those of ordinarily skilled in the relevant arts. It should also be understood that terminology employed herein is used for the purpose of describing particular embodiments only and is not intended to be limiting.

It must be noted that, as used in this specification and the appended claims, the singular forms "a" and "the" can include plural referents, unless the context clearly dictates otherwise. Thus, for example, reference to a "valve" can include reference to one or more of such valves.

DEFINITIONS

In describing and claiming the present invention, the following terminology will be used in accordance with the definitions set forth below.

Relative directional terms, such as "distal," "proximal," "upper," "lower," "top," "bottom," etc., are used herein to aid in describing various features of the present systems and techniques. It is to be understood that such terms are generally used in a manner consistent with the understanding one of ordinary skill in the art would have of such systems. Such terms should not, however, be construed to limit the present invention.

The term "fluid" is used herein in its broad sense, and can refer to a liquid or a gas, or combinations thereof.

As used herein, the term "substantially" refers to the complete, or nearly complete, extent or degree of an action, characteristic, property, state, structure, item, or result. As an arbitrary example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained.

The use of "substantially" is equally applicable when used in a negative connotation to refer to the complete or near complete lack of an action, characteristic, property, state, structure, item, or result. As another arbitrary example, a composition that is "substantially free of" particles would either completely lack particles, or so nearly completely lack particles that the effect would be the same as if it completely lacked particles. In other words, a composition that is "substantially free of" an ingredient or element may still actually contain such item as long as there is no measurable effect thereof.

As used herein, the term "about" is used to provide flexibility to a numerical range endpoint by providing that a given value may be "a little above" or "a little below" the endpoint.

Distances, forces, weights, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited.

As an illustration, a numerical range of "about 1 inch to about 5 inches" should be interpreted to include not only the explicitly recited values of about 1 inch to about 5 inches, but also include individual values and sub-ranges within the indicated range. Thus, included in this numerical range are individual values such as 2, 3, and 4 and sub-ranges such as from 1-3, from 2-4, and from 3-5, etc.

This same principle applies to ranges reciting only one numerical value and should apply regardless of the breadth of the range or the characteristics being described.

Invention

The present invention relates generally to surgical instruments suitable for use in a variety of surgical procedures, including thoracoscopy, laparoscopy, pelviscopy, endoscopy, and arthroscopy, and the like. While the present devices can be adapted for use in many of these different procedures, they are particularly well adapted for use in laparoscopic procedures. As such, the present discussion will focus primarily on their use in laparoscopy. It is to be understood, however, that the instruments and methods disclosed herein are not limited to laparoscopic applications.

During a typical laparoscopic surgical procedure, a small incision is made in a wall of a patient's abdomen to allow the introduction of a surgical implement into the patient's abdominal cavity. The surgical instrument can be of a variety of types, including instruments for cutting, suturing, clamping, grasping, cauterizing, etc., as well as devices that allow a surgeon to view the procedure (most commonly a video camera known as a laparoscope). The primary benefit of performing laparoscopy is that the procedure is considered minimally invasive due to the relatively small incision size required for the procedure. Typically, this incision size is from 0.5 to 1.5 cm. While such incisions are considerably smaller than those required for open procedures, incisions of even this small size can cause post operative problems, including unnecessary scarring.

Due to these and other considerations, professionals in field of laparoscopy continue to search for ways in which the size of the necessary incision can be reduced. While utilizing instruments with smaller diameters has been attempted, this reduction in size comes with a corresponding reduction in strength and stiffness. Thus, decreasing the size of the instrument used can increase the risk of bending of the instrument, which can increase the risk of damaging the instrument in the case of inelastic bending. Excessive bending can also contribute to outright breakage of instruments if they are rigid and bent beyond their elastic limit. Even in cases where the instrument bends elastically, the risk of damaging tissue within the patient is increased when severe bending occurs. For example, the kinetic energy stored within a flexed instrument can cause the instrument to inadvertently strike and damage tissue when the instrument is suddenly dislodged and the energy is released into motion.

The present system addresses these and other issues currently experienced in the endoscopic surgery field. A first embodiment of the invention is shown generally in FIGS. 1A through 1D, in various stages of assembly. Typically, the system will include one or more surgical instruments 12 which can be of a variety of types, such as laparoscopes, cutting devices, clamping devices (such as that shown), dissecting devices, etc. In the example shown, the clamping device 12 can include a distal end 16, which includes pincers for clamping tissue or organs. A proximal end can include handles 18 which allow a surgeon to operate the device. A body portion 20 is generally elongate and provides distance between the distal, working end and the proximal, handle end. A coupling interface 22 can also be provided that allows the surgical instrument to be attached to an oversleeve 14, either directly or indirectly, as will be discussed in more detail below.

The system can also include a protective oversleeve 14 through which the surgical instrument can be inserted. The oversleeve covers and protects the elongate midportion 20 of the instrument 12 while leaving the operable ends of the instrument exposed to function properly. The oversleeve can include a central, generally elongate rigid portion that supports the surgical device. A coupling interface 24 (FIG. 1C) can also be provided on the oversleeve to allow it to be coupled, either directly or indirectly, to the surgical device.

The oversleeve 14 can be much more rigid than is the surgical instrument such that the oversleeve prevents the instrument from bending to an undesirable degree. The oversleeve can be formed from a variety of materials, including, without limitation, stainless steel, ceramic titanium, titanium, etc. The oversleeve is typically sized with an internal bore that is only slightly larger than an outer diameter of the body portion 20 of the surgical instrument 12. The outer diameter of the oversleeve can vary, but is typically sized as small as possible while still providing the support needed for the instrument to be held within the oversleeve. In one exemplary embodiment, the oversleeve has an outer diameter of less than about 3 mm. Typically, the oversleeve will extend along (e.g., cover) more than about 95% of the body portion of the surgical instrument.

Many conventional laparoscopic procedures rely upon a stationary trocar system (not shown) that is installed within the abdominal wall. This type of system includes a cannula that remains stationary relative to the abdominal wall. Surgical instruments can be inserted through the cannula and manipulated within the abdominal cavity. As the cannula portion of the trocar system remains stationary (that is, it does not slide within the incision created for the cannula), the clearance between the inner diameter of the cannula and the outer diameter of the surgical instruments has to be great enough to allow relative movement between the two devices (i.e., to allow the surgical instruments to be manipulated within the cannula). This type of system, however, requires that the cannula not move during the surgical procedure.

In contrast, the oversleeves 14 of the present system are designed to be inserted directly through the incision formed within the abdominal wall, and can be moved (e.g., slid) relative to the incision as the operation is performed. While the oversleeve can move within the incision, there is some natural resistance to this motion due to the elasticity of the tissue in which the incision is formed. Thus, it is generally desirable to maintain the oversleeve in a fixed position over the surgical instrument 14, as otherwise movement of the surgical instrument may not result in movement of the oversleeve. The present system provides a variety of ways in which the oversleeve can be restricted from moving relative to the surgical instrument (and vice versa) while the surgical instrument is being used.

In the embodiments illustrated in FIGS. 1 through 1D, the system can include a canister assembly (sometimes referred to as a cannula body) 30 (FIG. 1A) that can be coupled to both the oversleeve 14 and to the surgical instrument 12. Note the oversleeve is typically coupled to the surgical instrument immediately adjacent the handle portion 18. As shown in FIGS. 1B, 1C and 1D, in one aspect of the invention the canister assembly can include two or more segments or end caps 32, 34 that can be coupleable one to another to form the canister. In the embodiment shown, the canister includes a distal segment 32 and a proximal segment 34 that are threadably coupleable to one another. A valve 36 can also be provided within the canister. The valve can limit or prevent the back-flow of fluids through the overall assembly to limit or prevent, for example, inflation gasses from prematurely escaping from the abdominal cavity.

While a variety of valves 36 can be provided, in the example shown, the valve is a "duck bill" valve that allows relatively easy insertion of the surgical instrument 12 through the valve, yet resists the passage of fluids in the other direction (e.g., in the direction toward the handle 18). The distal 32 and proximal 34 segments of the canister 30 can include geometry that allows the valve 36 to fit securely within the canister, or between end caps 32, 24 when properly positioned.

Thus, when the system shown is fully assembled (see, for example, FIG. 1A), the oversleeve 14 is coupled to the distal segment 32 of the canister 30, the distal segment 32 is coupled to the proximal segment 34 (with valve 36 contained therebetween), and the proximal segment 34 is coupled to the surgical instrument 12 adjacent the handle 18. In this manner, movement of the handle of the surgical instrument results in movement of the entire assembly.

The various components of the system can be joined together in a variety of ways. In many instances, threaded couplers can be used to make the connections, as will be appreciated by one of ordinary skill in the art having possession of this disclosure. While a wide range of threaded fastening systems can be employed, known systems such as the "Luer Lock" system can be utilized. In addition to threaded fastening systems, other mating interfaces can be utilized, such as a bayonet-style fittings, "Luer Slip" fittings, etc., twist-lock fittings, etc.

In the embodiments illustrated in the figures, the various threaded fittings are shown having a particular orientation. For example, in FIG. 1C, the coupling interface 24 of the oversleeve includes male threads that mate within corresponding female threads (not shown) of end cap or segment 32. End cap or segment 34 includes male threads that mate within corresponding female threads of end cap 32. End cap 34 also includes internal female threads, in this example, "Luer Lock" threads that mate with male "Luer Lock" threads on handle 18 (e.g., at coupling interface 22). It is to be understood that such configuration can be varied for various implementations to provide superior performance. For example, in one aspect of the invention, the threaded interface between the end cap 34 and the handle 18 can be altered such that the male threads are carried by end cap 34 and the female threads are carried by the handle 18. Various other changes can be made to the coupling structure, as any particular application dictates.

The canister or valve assembly 30 can also include a port 42 coupled thereto or formed therein. The port can include a cap 44, as is generally known by those of ordinary skill in the art (see, for example, FIG. 1B which shows cap 44 installed over port 42). The port can be positioned to allow the introduction of, or the evacuation of, fluids to or from the valve assembly. In the embodiment shown, the port is positioned on the distal side of valve 36 when the end caps 32, 34 and the valve 36 are assembled together. In this manner, when the components are assembled, fluid can be introduced into the valve assembly through port 42 and the valve 36 limits or prevents fluid from flowing toward the handle 18. However, the valve assembly allows the free flow of fluid out of the valve assembly and into an internal portion of the oversleeve 14. In this manner, fluid can flow through the oversleeve (and around the elongate body 20 of the surgical instrument 18) to allow the fluid to be introduced into a patient's anatomy. The same system can be used, if desired, to remove fluid from the surgical site, back through the port 42, through the use of suction.

The relative sizes of the various components of the surgical instruments 12, the oversleeve 14, the canister 30, etc., can vary depending upon the application and the type of surgical device. Generally speaking, however, the oversleeve can be provided in sizes ranging from an outside diameter of about 1.5 mm to about 3.0 mm, with an inside diameter of about 1.4 mm to about 2.9 mm. Similarly, the outside diameter of the surgical instrument can range from about 1.4 mm to about 2.9 mm. Typically, the outside diameter of the surgical instrument will be only slightly less than the inside diameter of the oversleeve, such that very little play exists between the two. The clearance between the two can range from about 0.05 mm to about 0.3 mm.

FIGS. 2A through 2D illustrate another embodiment 100 of the invention in which an alternate manner of restraining relative movement between the surgical instrument and the oversleeve is provided. While the embodiment of the invention described above uses a mating interface (threaded or otherwise) to secure the surgical instrument to the oversleeve, many existing surgical instruments do not include the necessary fittings to ensure this can be done properly. Thus, even though an existing surgical instrument 12' can benefit from the protection provided by oversleeve 14', it may not be possible to provide an oversleeve that easily mates with an existing surgical instrument. The present technology provides embodiments in which an interface can be provided between the two, using commonly found existing components.

For example, many existing surgical instruments include a port formed therewith through which a fluid (gas or liquid) can be introduced or vented. In the embodiment shown most clearly in FIGS. 2B and 2D, surgical instrument 12' includes a port 42 to which an auxiliary system (not shown) can be attached to allow the introduction of a fluid into or through the surgical device. It may be desired, for example, to introduce a fluid flow through a small bore (not shown) formed through surgical device 12' for purpose of inflation, irrigation, etc. These ports are typically provided with a cap 44 that is held by tether 46 adjacent the port when not in use (when in use, the cap is installed over the port 42—see, for example, the arrangement of cap and port in FIG. 1B).

The present technology provides a manner in which these known port and cap systems can be utilized to limit or prevent movement of the surgical instrument 12' relative to the oversleeve 14'. As shown for example in FIGS. 2A and 2B, in one aspect of the invention, the cap 44a intended for use on port 42a can instead be used to cap port 42 associated with the surgical instrument. In this manner, the tether 46a restrains movement of the oversleeve relative to the surgical instrument, even in the absence of a predesigned mating interface between the two devices. In practice, a medical practitioner can insert surgical device 12' through oversleeve 14', then secure cap 44a atop port 42, resulting in tether 46a securing the two devices together. It has been found that this interface, while allowing some play between the devices, is sufficient to limit relative movement between the two devices to allow proper use of the oversleeve system with suitably equipped existing surgical devices.

As also shown in FIGS. 2A, 2B and 2C, in the event the oversleeve includes a canister 30 having a port 42a associated therewith, two tethers can be utilized to provide an even greater securing force between the surgical instrument and the oversleeve. As best shown in FIG. 2B, cap 44 can be installed over port 42a, with cap 44a being installed over port 42. In this manner, both tethers 46 and 46a act to restrain or limit relative motion between the oversleeve and the surgical instrument. Also, both ports 42 and 42a can be properly capped when not in use.

Figure 3B:
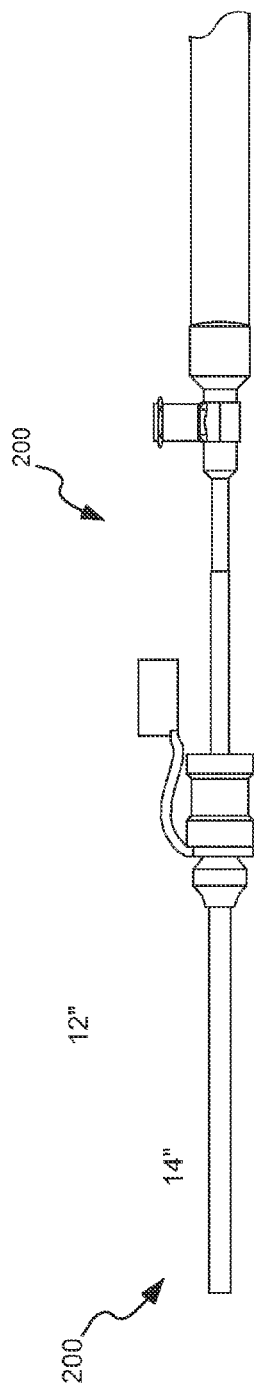
FIG. 3B is a partially sectioned and exploded view of the system of FIG. 3A.
Figure 3C:
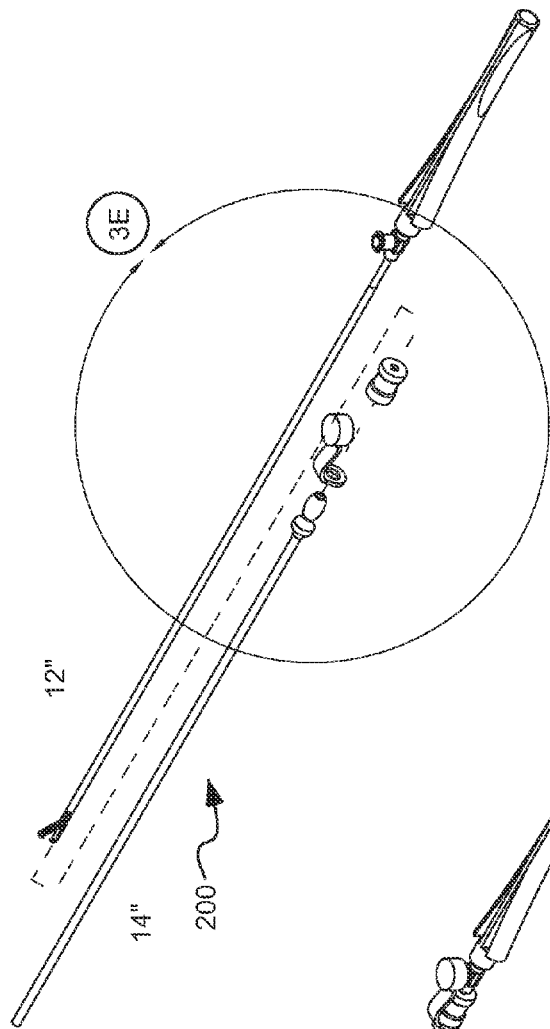
FIG. 3C is an exploded perspective view of the system of FIG. 3A.
Figure 3A:
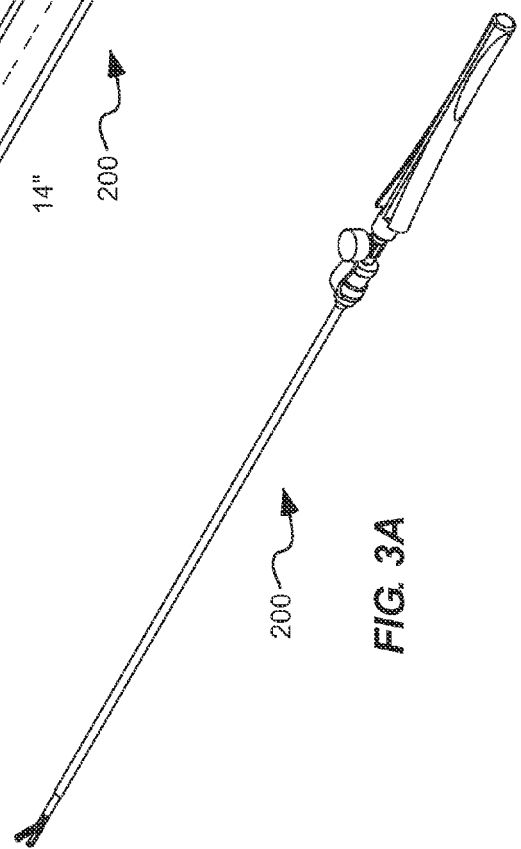
FIG. 3A is a perspective view of another exemplary surgical instrument system in accordance with an embodiment of the invention.

FIGS. 3A through 3E illustrate another embodiment 200 of the invention that can be utilized when oversleeve 14" and surgical instrument 12" either do not include mating interfaces, or have incompatible mating interfaces. That is, this system can be used when the oversleeve and the surgical instrument are not designed to be coupled to one another. In this embodiment, a gasket 50 can be attached to either the oversleeve 14" or the surgical instrument 12". The gasket can be formed of a resilient material that will elastically flex. As shown in FIG. 3D, an inside diameter $50_i$ of the gasket 50 can be formed smaller than an outside diameter $14''_o$ of the oversleeve (or a component of the oversleeve, as shown in FIG. 3E). Thus, when the oversleeve is inserted within the gasket (or the gasket inserted over the oversleeve), an elastic friction fit is created between the two.

A tether 46" can be used to provide a method by which the oversleeve 14" can be coupled to the surgical instrument 12". As best shown in FIG. 3E, the tether can be installed over the raised portion $14''_o$, after which the gasket 50 can be snugly installed on the raised portion. In this manner, the gasket secures the ring 54 of the tether to the oversleeve (it is essentially "sandwiched" between two components on the oversleeve). The cap portion 44" of the tether can then be installed on a port fitting 42" on the surgical device once the surgical device is installed within the oversleeve. The tether then serves to limit or prevent relative movement of the oversleeve and the surgical instrument. While the gasket 50 can be of a variety of forms, in one embodiment, the gasket 50 is a seal that can be relatively easily obtained, as it is used in other endoscopic applications to prevent the flow of fluids.

In addition to the structural system outlined above, the present technology provides various methods of utilizing the components shown and described for a number of uses. Methods of performing surgery on an animal can be provided, as can methods of assembling surgical systems, methods of restraining surgical instruments relative to protective oversleeves, methods of modifying existing surgical instruments, etc. Any such methods that would occur to one of ordinary skill in the art, having possession of this disclosure, are considered a part of this disclosure.

It is to be understood that the above-referenced arrangements are illustrative of the application for the principles of the present invention. Numerous modifications and alternative arrangements can be devised without departing from the spirit and scope of the present invention while the present invention has been shown in the drawings and described above in connection with the exemplary embodiments(s) of the invention. It will be apparent to those of ordinary skill in the art that numerous modifications can be made without departing from the principles and concepts of the invention as set forth in the examples.

The invention claimed is:

1. A minimally invasive surgical system, comprising:
   a surgical instrument having an elongate body portion;
   an oversleeve, positionable over the elongate body portion of the surgical instrument, the oversleeve being more rigid than the elongate body portion of the surgical instrument; and
   a valve assembly, associated with one of the oversleeve or the surgical instrument, the valve assembly including;
     first and second end caps removably coupleable to one another; and
     a valve positioned between the first and second end caps, the valve operable to limit or prevent flow of fluid from the valve assembly from one end cap when the end caps are coupled to one another;
     one of the end caps being removably coupleable to the surgical instrument, and another of the end caps being removably coupleable to the oversleeve;
   the valve assembly being operable to selectively prevent relative movement between the oversleeve and the surgical instrument and to allow fluid flow through the valve assembly and into an internal portion of the oversleeve; wherein
   the first and second end caps, the surgical instrument and the oversleeve are threadably coupleable to one another.

2. The system of claim 1, wherein the surgical instrument comprises a laparoscopic surgical instrument.

3. The system of claim 1, wherein the valve assembly includes a port coupled thereto, the port allowing the flow of fluid into or out of the valve assembly.

4. The system of claim 3, wherein the port is positioned relative to the valve such that fluid flowing through the port flows into the internal portion of the oversleeve.

* * * * *